(12) United States Patent
Bosslet et al.

(10) Patent No.: US 6,926,896 B2
(45) Date of Patent: Aug. 9, 2005

(54) MONOCLONAL ANTIBODIES (MABS) AGAINST TUMOR-ASSOCIATED ANTIGENS, THE PREPARATION AND USE THEREOF

(75) Inventors: Klaus Bosslet, Marburg (DE); Gerhard Seemann, Marburg (DE); Hans Harald Sedlacek, Marburg (DE); Bernhard Auerbach, Marburg (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 08/356,791

(22) Filed: Dec. 13, 1994

(65) Prior Publication Data

US 2002/0068056 A1 Jun. 6, 2002

Related U.S. Application Data

(63) Continuation of application No. 08/118,788, filed on Sep. 9, 1993, now abandoned, which is a continuation of application No. 07/949,359, filed on Sep. 23, 1992, now abandoned, which is a continuation of application No. 07/497,201, filed on Mar. 22, 1990, now abandoned.

(30) Foreign Application Priority Data

Mar. 24, 1989 (DE) ...................................... P 39 09 799

(51) Int. Cl.$^7$ ...................... A61K 39/395; C07K 16/30; C12P 21/08
(52) U.S. Cl. ................................ 424/155.1; 424/130.1; 424/133.1; 424/138.1; 424/141.1; 424/174.1; 424/178.1; 424/181.1; 435/69.6; 530/387.1; 530/387.3; 530/387.7; 530/388.1; 530/388.2; 530/388.8; 530/391.1; 530/391.7
(58) Field of Search ............................ 424/1.49, 130.1, 424/141.1, 178.1, 133.1, 155.1, 174.1; 435/69.6, 15.47, 172.2, 320.1; 530/387.1, 388.1, 391.1, 387.3, 388.8, 388.15, 391.7, 391.3, 387.7

(56) References Cited

U.S. PATENT DOCUMENTS

| | | | |
|---|---|---|---|
| 3,862,925 A | 1/1975 | Sarantakis et al. | |
| 4,331,647 A | 5/1982 | Goldenberg et al. | |
| 4,349,528 A | 9/1982 | Koprowski et al. | |
| 4,444,744 A | 4/1984 | Goldenberg | |
| 4,446,240 A | 5/1984 | Nerenberg | |
| 4,460,561 A | 7/1984 | Goldenberg | |
| 4,485,093 A | 11/1984 | Schlom et al. | |
| 4,522,918 A | 6/1985 | Trowbridge | |
| 4,569,788 A | 2/1986 | Mulshine et al. | |
| 4,579,827 A | 4/1986 | Sakamoto et al. | |
| 4,582,797 A | 4/1986 | Trowbridge | |
| 4,585,742 A | 4/1986 | Bernal | |
| 4,590,071 A | * 5/1986 | Scannon et al. | 424/85 |
| 4,612,282 A | 9/1986 | Schlom et al. | |
| 4,645,828 A | 2/1987 | Twardzik et al. | |
| 4,677,058 A | 6/1987 | Tryggvason et al. | |
| 4,683,200 A | 7/1987 | Hirohashi et al. | |
| 4,810,781 A | * 3/1989 | Hollinshead | 530/806 |
| 6,294,172 B1 | * 9/2001 | Bosslet et al. | |

FOREIGN PATENT DOCUMENTS

| | | |
|---|---|---|
| DE | 3329184 | 2/1985 |
| DE | 3329184 A1 | 2/1985 |
| EP | A 0118365 | 9/1975 |
| EP | A 0098162 | 1/1984 |
| EP | 0 141 079 | 5/1985 |
| EP | A0141079 | 5/1985 |
| EP | 0145373 A3 | 6/1985 |
| EP | 0151030 A2 | 8/1985 |
| EP | A0153114 | 8/1985 |
| EP | A0160446 | 11/1985 |
| EP | 0160897 A2 | 11/1985 |
| EP | 0171083 A3 | 2/1986 |
| EP | 0189849 A2 | 8/1986 |
| EP | A-0213581 | 3/1987 |
| EP | 0268468 A2 | 5/1988 |
| EP | 0 268 468 | 5/1988 |
| EP | 0 365 209 | 4/1990 |
| EP | 0 368 684 | 5/1990 |
| EP | 0 411 893 A2 | 2/1991 |
| GB | 1193378 | 5/1970 |
| WO | WO-A8101469 | 5/1981 |
| WO | WO 88/02117 | 3/1988 |

OTHER PUBLICATIONS

Waiduam, T (1991) Science 252: 1657–1662.*
ATCC Catalog (7th ed.; 1992) R. Hay et al, "Turner Index", pp. 485–491.*
Sun et al (1987) Proc. Nat'l Acad Sci 54:214–218.*
Shaw et al (1987) J. Immunol. 12 138: 4534–4538.*
Sakagan et al (1986) J. Immunol. 137: 1066–1074.*
Hnatowick et al (1983) Science 220: 613–615.*
Gallagher et al (1986) J. Surg. Res. 40: 159–166.*
Vitetta et al (1987) Science 238: 1098–1104.*
Bosslet et al (1956) Cancer Immunol Immunother. 23: 185–191.*
Bosslet et al (1959) Cancer Immunol Immunother. 29: 171–178.*
Chung et al (1987) Cancer 60: 1636–1643.*
Steplewski et al (1988) PNAS 85: 4852–4856.*
Colcher et al (1989) Cancer Res. 49: 1738–1745.*
Reichmann et al. (1988) Nature 332: 323–327.*
Talalay, P., et al., "Chromogenic Substrates, II. Phenolphthalein Glucuronic Acid as Substrate for the Assay of Glucuronidase Activity," J. Biol. Chem., 166:757–772 (1946).

(Continued)

*Primary Examiner*—Phillip Gambel
(74) *Attorney, Agent, or Firm*—Finnegan, Henderson, Farabow, Garrett & Dunner, L.L.P.

(57) ABSTRACT

The invention relates to murine monoclonal antibodies (MAbs), A, B, C and D, which are directed against tumor-associated antigens. The nearly complete nucleotide sequences of the V genes of these MAbs are described, so that the relevant variable domains can be put together to give chimeric MAbs, or "humanized" MAbs are obtained by inserting the hypervariable regions (complementarity determining regions=CDR) into a human MAb framework. Antibody constructs of this type can be employed in human therapy and in vivo diagnosis without the disadvantages observed with murine MAbs.

10 Claims, 6 Drawing Sheets

OTHER PUBLICATIONS

Conchie, J., et al., "Mammalian Glycosidases, Distribution in the Body," Biochem., 71:318–325 (1959).

Davies, P., et al., "The Quantitative Estimation of Pinocytosis Using Radioactive Coloidal Gold," Biochemical and Biophysical Research Communications, 52(2):627–634 (1973).

Lieber, M. et al., Establishment of a Continuous Tumor–Cell Line (PANC–1) From a Human Carcinoma of the Exocrine Pancreas, Int. Cancer, 15:741–747 (1975).

Bosslet, K., et al., "Monoclonal Murine Antibodies with Specificity for Tissue Culture Lines of Human Squamous–Cell Carcinoma of the Lung," Cancer Detection and Prevention, 6:181–184 (1983).

Herlyn, D., et al., "Inhibition of Human Tumor Growth by IgG2a Monoclonal Antibodies Correlates with Antibody Density on Tumor Cells," J. Immunology, 134(2):1300–1304 (Feb. 1985).

Brown J., et al., "A Microassay for Antibody Binding to Tumor Cell Surface Antigens Using $^{125}$–Labelled Protein A from Staphylococcus Aureus," J. Immunological Methods, 15:57–66 (1977).

Heyderman, E., "Immunoperoxidase Technique in Histopathology: Applications, Methods and Controls," J. Clinical Pathology, 32:971–978 (1979).

Bosslet, K., et al., "Molecular Characteristics of Two Lung Carcinoma Cell–Line Associated Membrane Antigens," Behring Inst. Mitt, 74:27–34 (1984).

Meeting Highlights, "Breast Cancer, Epithelial Cells, and Extracellular Matrix," JNCI, 73(4):9099–1001 (Oct. 1984).

Wilson, B., et al., "Human Melanoma–associated Antigens Identified with Monoclonal Antibodies," La Ricerca Clin. Lab., 12:517–538 (1982).

Loop, S., et al., "Human Tumor–asociated Antigens, p155 and p210, Detected by Monoclonal Antibodies," Biological Abstracts, vol. 73, Heft 1, p. 431, column 2, Abstract No. 4132 (1982); abstract, Int. J. Cancer, 27(6):775–782 (1981).

Wilson, B., et al., "Distribution and Molecular Characterization of a Cell–Surface and a Cytoplasmic Antigen Detectable in Human Melanoma Cells with Monoclonal Antibodies," Abstract, Int. J. Cancer, Band 28, pp. 293–300 (1981), abstract, p. 293.

Johnson, J., et al., "Surface Antigens of Human Melanoma Cells Defined by Monoclonal Antibodies, I. Biochemical Characterization of Two Antigens found on Cell Lines and Fresh Tumors of Diverse Tissue Origin," Eur. Journal Immunology, 11:825–831 (1981).

Houghton, A., et al., "surface Antigens of Melanocytes and Melanomas," J. Exp. Med., 156:1755–1766 (19820.

Klapdor, R., et al., "Experimental and Clinical Studies with the New Monoclonal Antibody 494132 in Pancreatic Carcinomas," Digestion, 35(1) 1986.

Mitchell, K., "A Carcinoembryonic Antigen (CEA) Specific Monoclonal Hybridoma Antibody that Reacts only with High–Molecular–Weight CEA," Chemical Abstracts, 94(17):577, abstract no. 137538s (1981).

Accolla, R., et al., "Monoclonal Antibodies Specific for Carcinoembryonic Antigen and Produced by Two Hybrid Cell Lines," Proc. Natl Acad. Sci. (USA), 77(1):563–566 (1980).

Wunderlich, M., et al., "Effects or Adjuvant Chemo–or Immunotherapy on the Prognosis of Colorectoal Cancer Operated for Cure," Br. J. Surg. Suppl.:S107–S110 (1985).

Morrison–Plummer, et al., Journal of Immunological Methods, 64:165–178 (1983).

Cuttitta, et al., Proc. Natl. Acad. Sci., 78(7):4591–4595 (1981).

Kohler, et al., Nature, 256:495–497 (1975).

Hand, et al., Cancer Research, 45:833–840 (1985).

Magnani, et al., Cancer Research, 43:5489–5492 (1983).

Wise, et al., Infection and Immunity, 41(3):1332–1339 (1983).

Waldmann, Science, 252:1657–1662 (1991).

Harris et al., TIBTECH, 11:42–46.

Osband et al., Immunotherapy, 11:193–195 (1990).

Dillman, Ann. Internal. Med., 111:592–603 (1989).

Hird et al., Genes and Cancer, published 1990 by Wiley & Sons Ltd. 17, ed. Carnet et al.

Schmiegal, et al., Cancer Research, 45:1402–1407 (1985).

Chin, et al., Cancer Research, 45:1723–1729 (1985).

Yuan, et al., Cancer Research, 45:6179–6187 (1985).

Campbell, Monoclonal Antibody Technology, chapters 3, 4 and 6 to 10 (Cold Spring Harbor, 1985).

Kohler et al., Eur. J. Immunol., 6:511–519 (1976).

Bosslet et al., Br. J. Cancer, 56(4):516 (1987).

Schulz et al., Br. J. Cancer, 56(4):526 (1987).

Kubel et al., Br. J. Cancer, 56(4):528 (1987).

Campbell, Monoclonal Antibody Technology, pp. 67–101, 120–177, and 180–215 (Elsevier) (1985).

Lutz Riechmann et al., "Reshaping human antibodies for therapy," Feb. 1988, Nature Vol. 332, pp. 323–327.

Peter Lind et al., "Anti–Carcinoembryonic Antigen Immunoscintigraphy (Technetium–99m–Monoclonal Antibody BW 431/26) and Serum CEA Levels in in Patients with Suspected Primary and Recurrent Colorectal Carcinoma," Jul. 1991, The Journal of Nuclear Medicine, vol. 32, No. 7, pp. 1319–1325.

P. Benz et al., "Monoclonal antibody BW 431/26 labelled with technetium 99m and indium 111: an investigation of the biodistribution and the diosimetry in patients," May 1991, Nuclear Medicine vol. 18, No. 10, pp. 813–816.

Peter Lind et al., "Immunoscintigraphy of Inflammatory Processes with a Technetium–99m–Labeled Monoclonal Antigranulocyte Antibody (Mab BW 250/183)," Apr. 1990, The Journal of Nuclear Medicine vol. 31, No. 4, pp. 417–423.

Cahan, L., et al., "Identification of a Human Nueoectodermal Tumor Antigen (OFA–I–2) as Ganglioside GD2," Proc. Natl. Acad. Sci. USA, 79: 7629–7633 (1982).

Saito, M., et al., "Ganglioside GD2 Specificity of Monoclonal Antibodies to Human Neuroblastoma Cell," Biochemical and Biophysical Research Communications, 127(1): 1–7 (1985).

English Language Translation of DE 3329184A1.

Rodger Staden, "The Current Status and Portability of Our Sequence Handling Software", vol. 14, No. 1 (1986) pp. 217–231.

Randall K. Saiki et al., Enzymatic Amplification of β–Globin Genomic Sequences and Restriction Site Analysis for Diagnosis of Sickle Cell Anemia, Science 230, 1350–1354 (1985).

Sanger et al., "DNA sequencing with Chain–Terminating Inhibitors," Natl. Acad. Sci. USa, vol. 74, No. 12, pp. 5463–5467, Dec. 1977.

Martine Verhoeyen, et al., "Reshaping Human Antibodies: Grafting an Antilysozyme Activity," Science, vol. 239, 1534–1536, 1987

* cited by examiner

MAb A
VH

```
  Q   V   Q   L   Q   E   S   G   G   G   L   V   Q   P   G   G   S   L   R   L
CAGGTCCAACTGCAGGAGTCTGGAGGAGGCTTGGTACAGCCTGGGGGTTCTCTGAGACTC
       10          20          30          40          50          60

S   C   A   T   S   G   F   S   D   Y   Y   M   N   W   V   R   Q   P   P   G
TCCTGCGCAACTTCTGGGTTCAGTGATTACTACATGAACTGGGTCCGCCAGCCTCCAGGA
       70          80          90         100         110         120

K   A   L   E   W   L   G   F   I   S   N   K   P   N   G   H   T   T   E   Y
AAAGCACTTGAGTGGTTGGGTTTTATTTCAAACAAACCTAATGGTCACACAACAGAGTAC
      130         140         150         160         170         180

S   A   S   V   K   G   R   F   T   I   S   R   D   N   S   Q   S   I   L   Y
AGTGCATCTGTGAAGGGTCGGTTCACCATCTCCAGAGATAATTCCCAAAGCATCCTCTAT
      190         200         210         220         230         240

L   Q   M   N   T   L   R   A   E   D   S   A   T   Y   Y   C   A   R   D   K
CTTCAAATGAACACCCTGAGAGCTGAGGACAGTGCCACTTATTATTGTGCAAGAGATAAG
      250         260         270         280         290         300

G   I   R   W   Y   F   D   V   W   G   Q   G   T   T   V   T   V   S   S
GGAATACGATGGTACTTCGATGTCTGGGGCCAAGGGACCACGGTCACCGTCTCCTCA
      310         320         330         340         350
```

MAb A
VK

```
  A   I   L   S   A   S   P   G   E   K   V   T   M   T   C   R   A   S   S   S
AGCAATCCTGTCTGCATCTCCAGGGGAGAAGGTCACAATGACTTGCAGGGCCAGCTCAAG
       10          20          30          40          50          60

V   S   Y   M   H   W   Y   Q   Q   K   P   G   S   S   P   K   P   W   I   Y
TGTAAGTTACATGCACTGGTACCAGCAGAAGCCAGGATCCTCCCCCAAACCCTGGATTTA
       70          80          90         100         110         120

A   T   S   N   L   A   S   G   V   P   A   R   F   S   G   S   G   S   G   T
TGCCACATCCAACCTGGCTTCTGGAGTCCCTGCTCGCTTCAGTGGCAGTGGGTCTGGGAC
      130         140         150         160         170         180

S   Y   S   L   T   I   I   R   V   E   A   E   D   A   A   T   Y   Y   C   Q
CTCTTACTCTCTCACAATCATCAGAGTGGAGGCTGAAGATGCTGCCACTTATTACTGCCA
      190         200         210         220         230         240

Q   W   S   S   N   P   L   T   F   G   A   G   T   K   L   E   I
GCAGTGGAGTAGTAACCCGCTCACGTTCGGTGCTGGGACCAAGCTGGAGATC
      250         260         270         280         290
```

Fig. 4

MAb B
VH

```
  L   Q   E   S   G   P   D   L   V   K   P   S   Q   S   L   S   L   T   C   T
CTGCAGGAGTCAGGACCTGACCTGGTGAAACCTTCTCAGTCACTTTCACTCACCTGCACT
       10        20        30        40        50        60

V   T   G   Y   S   I   T   S   G   Y   S   W   H   W   I   R   Q   F   P   G
GTCACTGGCTACTCCATCACCAGTGGTTATAGCTGGCACTGGATCCGGCAGTTTCCAGGA
       70        80        90       100       110       120

N   K   L   E   W   M   G   Y   I   Q   Y   S   G   I   T   N   Y   N   P   S
AACAAACTGGAATGGATGGGCTACATACAGTACAGTGGTATCACTAACTACAACCCCTCT
      130       140       150       160       170       180

L   K   S   R   I   S   I   T   R   D   T   S   K   N   Q   F   F   L   Q   L
CTCAAAAGTCGAATCTCTATCACTCGAGACACATCCAAGAACCAGTTCTTCCTGCAGTTG
      190       200       210       220       230       240

N   S   V   T   T   E   D   T   A   T   Y   Y   C   A   R   E   D   Y   D   Y
AATTCAGTGACTACTGAGGACACAGCCACATATTACTGTGCAAGAGAAGACTATGATTAC
      250       260       270       280       290       300

H   W   Y   F   D   V   W   G   A   G   T   T   V   T   V   S   S
CACTGGTACTTCGATGTCTGGGGCGCAGGGACCACGGTCACCGTCTCCTCA
      310       320       330       340       350
```

MAb B
VK

```
  L   T   Q   S   P   A   I   M   S   A   S   L   G   E   E   I   T   L   T   C
CTGACCCAGTCTCCAGCAATCATGTCTGCATCTCTAGGGGAGGAGATCACCCTAACCTGC
       10        20        30        40        50        60

S   T   S   S   S   V   S   Y   M   H   W   Y   Q   Q   K   S   G   T   S   P
AGTACCAGCTCGAGTGTAAGTTACATGCACTGGTACCAGCAGAAGTCAGGCACTTCTCCC
       70        80        90       100       110       120

K   L   L   I   Y   S   T   S   N   L   A   S   G   V   P   S   R   F   S   G
AAACTCTTGATTTATAGCACATCCAACCTGGCTTCTGGAGTCCCTTCTCGCTTCAGTGGC
      130       140       150       160       170       180

S   G   S   G   T   F   Y   S   L   T   I   S   S   V   E   A   E   D   A   A
AGTGGGTCTGGGACCTTTTATTCTCTCACAATCAGCAGTGTGGAGGCTGAAGATGCTGCC
      190       200       210       220       230       240

D   Y   Y   C   H   Q   W   S   S   Y   P   T   F   G   G   G   T   K   L   E
GATTATTACTGCCATCAGTGGAGTAGTTATCCCACGTTCGGAGGGGGGACCAAGCTGGAG
      250       260       270       280       290       300
```

Fig. 5

MAb C
VH

```
  Q   V   Q   L   Q   Q   S   G   P   E   L   V   K   P   G   A   S   V   K   M
CAGGTCCAACTGCAGCAGTCTGGACCTGAGCTGGTAAAGCCTGGGGCTTCAGTGAAGATG
        10        20        30        40        50        60

S   C   K   A   S   G   Y   T   F   T   Y   Y   V   I   H   W   V   K   Q   K
TCCTGCAAGGCTTCTGGATACACATTCACTTACTATGTTATTCACTGGGTGAAACAGAAG
        70        80        90       100       110       120

P   G   Q   G   L   E   W   I   G   Y   I   H   P   Y   N   A   G   T   E   Y
CCTGGGCAGGGCCTTGAGTGGATTGGATACATTCATCCTTACAATGCTGGTACTGAGTAC
       130       140       150       160       170       180

N   E   K   F   K   G   K   A   T   L   T   S   D   K   S   S   S   T   A   Y
AATGAGAAGTTCAAAGGCAAGGCCACACTGACTTCAGACAAATCCTCCAGCACAGCCTAC
       190       200       210       220       230       240

M   E   L   S   S   L   T   S   E   D   S   A   V   Y   Y   C   S   M   G   R
ATGGAGCTCAGCAGCCTGACCTCTGAGGACTCTGCGGTCTATTACTGTTCAATGGGACGA
       250       260       270       280       290       300

G   G   D   Y   W   G   Q   G   T   T   V   T   V   S   S
GGGGGTGACTACTGGGGCCAAGGGACCACGGTCACCGTCTCCTCA
       310       320       330       340
```

MAb C
VK

```
  L   T   Q   S   P   A   I   M   S   A   S   P   G   E   K   V   T   M   T   C
CTGACCCAGTCTCCAGCAATTATGTCTGCATCTCCTGGGGAGAAGGTCACCATGACCTGC
        10        20        30        40        50        60

S   A   S   S   S   V   S   Y   M   H   W   Y   Q   Q   K   S   G   T   S   P
AGTGCCAGCTCAAGTGTAAGTTACATGCACTGGTACCAGCAGAAGTCAGGCACCTCCCCC
        70        80        90       100       110       120

K   R   W   I   Y   D   T   S   K   L   A   S   G   V   P   A   R   F   S   G
AAAAGATGGATTTATGACACATCCAAACTGGCTTCTGGAGTCCCTGCTCGCTTCAGTGGC
       130       140       150       160       170       180

S   G   S   G   T   S   Y   S   L   T   I   S   S   M   E   A   E   D   A   A
AGTGGGTCTGGGACCTCTTACTCTCTCACAATCAGCAGCATGGAGGCTGAAGATGCTGCC
       190       200       210       220       230       240

T   Y   Y   C   Q   Q   W   S   S   N   P   F   T   F   G   A   G   T   K   L
ACTTATTACTGCCAGCAGTGGAGTAGTAACCCATTCACGTTCGGCGCGGGGACCAAGCTG
       250       260       270       280       290       300

E   I
GAGATC
```

Fig. 6

VH    MAb D

```
 A   E   S   G   P   G   L   V   R   L   T   S   L   S   I   T   C   T   V   S
GCAGAGTCAGGGCCTGGCCTGGTGCGCCTCACGAGCCTGTCCATCACTTGCACTGTCTCT
        10        20        30        40        50        60

G   F   S   L   I   S   Y   G   V   H   W   V   R   Q   P   P   G   K   G   L
GGCTTTTCATTAATTAGTTATGGTGTACACTGGGTTCGCCAGCCTCCAGGAAAGGGTCTG
        70        80        90       100       110       120

E   W   L   G   V   I   W   A   G   G   S   T   N   Y   N   S   A   L   M   S
GAGTGGCTGGGAGTAATATGGGCAGGTGGAAGCACAAATTATAATTCGGCTCTCATGTCC
       130       140       150       160       170       180

R   L   S   I   S   K   D   N   S   K   S   Q   V   F   L   K   M   N   S   L
AGACTGAGCATCAGCAAAGACAACTCCAAGAGCCAAGTTTTCTTAAAAATGAACAGTCTG
       190       200       210       220       230       240

Q   T   G   D   T   A   I   Y   Y   C   A   R   G   G   D   D   Y   D   G   F
CAAACTGGTGACACAGCCATATACTACTGTGCCAGAGGGGGGGATGATTACGATGGGTTT
       250       260       270       280       290       300

A   Y   W   G   Q   G   T   T   V   T   V   S   S   G   E   S
GCTTACTGGGGCCAAGGGACCACGGTCACCGTCTCCTCAGGTGAGTCC
       310       320       330       340
```

MAb D

VK

```
 L   A   Q   S   T   K   R   K   N   Y   L   A   W   Y   Q   Q   K   P   G   Q
TCTGGCTCAGAGTACAAAGCGAAAGAACTACTTGGCTTGGTACCAGCAGAAACCAGGTCA
        10        20        30        40        50        60

S   P   K   L   L   I   Y   W   A   S   T   R   E   S   G   V   P   D   R   F
GTCTCCTAAACTACTGATCTACTGGGCATCCACTCGGGAATCTGGGGTCCCTGATCGCTT
        70        80        90       100       110       120

T   G   S   G   S   G   T   D   F   T   L   T   I   S   S   V   Q   A   E   D
CACAGGCAGTGGATCTGGGACAGATTTCACTCTCACCATCAGCAGTGTGCAGGCTGAAGA
       130       140       150       160       170       180

L   A   V   Y   Y   C   K   Q   S   Y   N   L   R   A   F   G   G   G   T   K
CCTGGCAGTTTATTACTGCAAACAATCTTATAATCTTCGGGCGTTCGGTGGAGGGACCAA
       190       200       210       220       230       240

L   E   I   K
GCTGGAGATCAAA
       250
```

MONOCLONAL ANTIBODIES (MABS) AGAINST TUMOR-ASSOCIATED ANTIGENS, THE PREPARATION AND USE THEREOF

CROSS-REFERENCES TO RELATED APPLICATIONS

This application is a continuation of application Ser. No. 08/118,788, filed Sep. 9, 1993, now abandoned, which is a continuation of application Ser. No. 07/949,359, filed on Sep. 23, 1992, now abandoned, which is a continuation of application Ser. No. 07/497,201, filed on Mar. 22, 1990, now abandoned, which is based on German Application Ser. No. P3909799.4, filed on Mar. 24, 1989.

STATEMENT OF FEDERALLY SPONSORED RESEARCH OR DEVELOPMENT

Not applicable.

BACKGROUND OF THE INVENTION

The invention relates to murine monoclonal a tibodies (MAbs), A, B, C and D, which are directed against tumor-associated antigens. The nearly complete nucleotide sequences of the V genes of these MAbs are described, so that the relevant variable domains can be put together to give chimeric MAbs, or "humanized" MAbs are obtained by inserting the hypervariable regions (complementarity determining regions CDR) into a human MAb framework. Antibody constructs of this type can be employed in human therapy and in vivo diagnosis without the disadvantages observed with murine MAbs.

MAb A reacts with antigen 2, MAb B reacts with antigen 11 and MAb C reacts with antigen 7, all of which are described in EP-A2 0,141,079 and are membrane-associated antigens on permanent human tumor cells lines such as the CaLu-1, Chago, Oat 75, PaTuII and Bewo cell line. MAb D is directed against a Vibrio cholerae neuraminidase (VCN)-sensitive epitope on the ganglioside $GD_2$ which is exposed on human melanoma cell lines.

MAbs A to D were generated as described in EP-A2 0,141,079 and isolated by standard methods.

MAb A binds to cells of the granulocyte compartment and to carcinomas of the colon, pancreas and some of the lung and breast, as shown in Tab. 1.

TABLE 1

Binding characteristics of MAb A

| Malignant tissue samples investigated | Number of positives | Total number |
|---|---|---|
| colorectal carcinomas: | | |
| primary carcinomas | 6 | 6 |
| liver metastases | 15 | 16 |
| carcinomas of the pancreas | 6 | 8 |
| carcinomas of the lung: | | |
| small-cell | 1 | 2 |
| adeno | 9 | 10 |
| squamous cell | 3 | 4 |
| large-cell | 1 | 2 |
| carcinoma of the breast | 1 | 3 |

MAb B binds to virtually all carcinomas of the gastrointestinal tract and to some ovarian carcinomas and adenocarcinomas of the lung, whereas it does not react with most normal human tissues or reacts only with secretion-containing sites thereon. The binding characteristics are summarized in Tab. 2.

TABLE 2

Binding characteristics of MAb B

| Malignant tissue samples investigated | Number of positives | Total number |
|---|---|---|
| colorectal carcinomas: | | |
| primary | 6 | 6 |
| liver metastases | 9 | 10 |
| carcinomas of the pancreas | 5 | 6 |
| carcinomas of the stomach | 4 | 4 |
| carcinomas of the lung: | | |
| small-cell | 2 | 11 |
| adeno | 9 | 10 |
| squamous cell | 2 | 12 |
| large-cell | 4* | 12 |
| carcinoma of the breast | 2 | 9 |
| ovarian carcinomas (secretion-containing sites) | 4 | 6 |
| carcinomas of the kidneys | 1 | 12 |

*weak, heterogeneous reaction

MAb C shows a distinct reaction with 70–80% of stage I and II primary tumors of carcinoma of the pancreas (11/14). Like the primary tumors, most grade I and II metastases of carcinoma of the pancreas appear to have a positive reaction (3/4). The type of reaction on these positive tissues indicates that the epitope recognized by MAb C is located in the cytoplasm, on the membrane and in the intercellular space.

Grade III carcinomas of the pancreas do not express the epitope (primary tumor 0/2, metastases 0/5). However, since grade I and II carcinomas of the pancreas comprise up to 95% of carcinomas of the pancreas, MAb C ought to react with 60–70% of all carcinomas of the pancreas.

Another important property of MAb C is its reactivity with the duct system in the chronically inflamed pancreas (pancreatitis 10/13), whereas there is no detectable binding to healthy exocrine and endocrine pancreatic tissue (0/8). Only a minority of the investigated primary tumors of carcinoma of the colon was reactive (4/14), whereas most of the liver metastases of carcinoma of the colon showed distinct binding (7/10).

Cross-reactivities of MAb C are confined to the mucus-producing goblet cells of the colonic mucosa and of the stomach. All the other normal tissue tested, including peripheral blood leukocytes and bone marrow, do not express the mucus-associated epitope recognized by MAb C (see Tab. 3). MAb C recognizes an epitope located on a tumor associated antigen which can be detected at increased levels in patients with gastrointestinal tumors e.g. carcinomas of the pancreas and thus may be used as a tumor marker.

TABLE 3

Summary of the formaldehyde-fixed, paraffin-embedded human tissue investigated (indirect immunoperoxidase) with MAb C.

| Pancreatic tumors | Grade I/II | Grade III |
|---|---|---|
| primary carcinoma | 11/14 | 0/2 |
| liver metastases of carcinoma | 3/4 | 0/5 |
| papillary carcinoma | 1/2 | |
| cystadenoma | 0/1 | |

TABLE 3-continued

Summary of the formaldehyde-fixed, paraffin-embedded human tissue investigated (indirect immunoperoxidase) with MAb C.

| Pancreatic tumors | Grade I/II | Grade III |
|---|---|---|
| Pancreatic tissue | | |
| ducts with changes due to pancreatitis | 10/13 | |
| normal exo- and endocrine pancreas | 0/8 | |
| Carcinomas of the colon | | |
| primary tumors | 4/14 | |
| liver metastases | 7/10 | |
| Normal colonic tissue | | |
| goblet cells of the mucosa, luminal part | 9/10 | |
| part of the mucosa facing the muscularis | 3/10 | |
| muscularis mucosae | 0/7 | |
| tunica muscularis | 0/7 | |
| submucosa | 0/7 | |
| Carcinomas of the lung | 8/18 (a few tumor cells) | |
| Carcinomas of the breast | 0/3 | |
| Other normal tissue investigated | | |
| lung | 0/3 | |
| liver | 0/5 | |
| breast | 0/1 | |
| Stomach | | |
| muscle | 0/2 | |
| mucus-prod. cells | 3/3 | |
| kidney | 0/5 | |
| lymph nodes | 0/4 | |
| spleen | 0/2 | |
| bone marrow | 0/1 | |
| peripheral blood leukocytes | 0/2 | |
| connective tissue | 0/2 | |
| muscles | 0/10 | |

MAb D recognizes a VCN-sensitive epitope on the ganglioside $GD_2$ which does not occur on other bovine cerebral gangliosides, including $GD_3$, $GM_3$, $GM_1$, $GT_{1a}$, $GD_{1b}$, $GD_{1a}$ and $GM_4$. Using MAb D it was possible to stain all gliomas, meningiomas and neurilemmomas in normal human cerebral tissue. Tab. 4 summarizes the binding properties of MAb D with respect to intracranial tumors.

TABLE 4

| | Number of tumors | |
|---|---|---|
| Type of tumor | Positive | Total number |
| well-differentiated gliomas, grade I–II | 6 | 6 |
| malignant gliomas, grade III–IV | 10 | 10 |
| meningiomas | 11 | 11 |
| neurilemmomas | 4 | 4 |
| pineal adenomas | 0 | 5 |
| metastases of carcinomas | 0 | 1 |

The epitope defined by MAb D is also present on neuroblastomas, ganglioneuroblastomas and ganglioneuromas. Tab. 5 shows a summary.

TABLE 5

Reactivity of MAb D with neuroblastomas and small round-cell tumors in children

| | Number of tumors | |
|---|---|---|
| Neuroblastomas | Positive | Total number |
| Grade I | 1 | 1 |
| Grade II | 6 | 6 |
| Grade III | 4 | 4 |
| ganglioneuroblastomas | 3[xx] | 3 |
| Ewing sarcomas | 0 | 2 |
| rhabdomyosarcomas | 0 | 1 |
| non-Hodgkin lymphomas | 2[xxx] | 5 |

[x]Hughes classification
[xx]ganglion cells
[xxx]some positive tumor cells

Thus, MAb D is suitable for differential diagnosis of neuroblastomas and small round-cell tumors in children.

The specificity of MAb D for two other tumors derived from the neuroectoderm, namely melanomas and small-cell carcinomas of the lung (SCLC), and for unrelated tumors is shown in Tab. 6.

TABLE 6

| | Number of tumors | |
|---|---|---|
| | Positive | Total number |
| melanoma | 4* | 10 |
| SCLC | 2* | 11 |
| carcinomas of the colon | 0 | 3 |
| carcinomas of the breast | 0 | 3 |
| non-SCLC: | | |
| adenocarcinomas | 0 | 3 |
| squamous cell carcinomas of the lung | 0 | 3 |
| large-cell carcinomas | 0 | 3 |

*Weak and heterogeneous staining of a few tumor cells

The immunoglobulin V genes of MAb A to MAb D were isolated using the methods detailed in the Examples.

The nucleotide and protein sequences are shown in Tables 7 (V gene of MAb A), 8 (V gene of MAb B), 9 (V gene of MAb C) and 10 (V gene of MAb D). The CDRs can be identified therein as described by Kabat and Wu (loc. cit., see Examples).

BRIEF SUMMARY OF THE INVENTION

Accordingly, the invention relates to the epitopes specified by MAbs A, B, C and D, monoclonal antibodies against these epitopes, with MAbs A, B, C and D being particularly preferred, and monoclonal antibodies which contain the V genes specified above, or parts thereof (complementarity determining regions), with a human antibody framework or framework parts being preferred. The invention furthermore relates to constructs which contain these V genes or parts thereof together with enzymes or radioactive labels or toxins or catalytic antibodies or combinations of various V-gene specificities or MHC class I or class II antigens or cytolytic components. Finally the invention relates to pharmaceuticals containing the MAb's specified above and the use of said MAb's or in vivo or in vitro diagnosis. The invention is furthermore contained in the Examples and the patent claims.

BRIEF DESCRIPTION OF THE DRAWINGS

FIG. 1, Detection of different antigens by Mab C. NS signifies serum samples of healthy blood donors (n=141);

AP means serum samples of patients with acute pancreatitis (n=56). CP means serum samples of patients with chronic pancreatitis (n=40) and Pan-Ca means patients with carcinoma of the pancreas (n=82). A means absorbance.

DETAILED DESCRIPTION OF THE INVENTION

EXAMPLES

The polymerase chain reaction (PCR) described by Saiki et al., Science 230, 1350–1354 (1985) was employed hereinafter for the cloning and expression of the variable domain of murine immunoglobulins (Ig).

1. Identification of the Conserved Regions at the 5' and 3' End of the Murine Heavy Ig Chain (VH) and the Light Ig Chain (VK).

The mutually aligned sequences of the variable regions were taken from the data file of Kabat et al. Sequences of Proteins of Immunological Interest, US Dept. of Health and Human Services, US Government Printing Office (1987). The nucleotide sequences start there at the amino terminus of the mature protein and do not include the signal sequences. Computer screening (DBUTIL, R. Staden (1986) Nucleic Acids Res. 14, 217–231) was used to find suitable primers for cDNA synthesis and amplimers for use in the PCR:

```
Oligonucleotide I:

Bst EII                VH1FORWARD
5' TGA GGA GAC GGT GAC CGT GGT CCC TTG GCC CCA 3'

Oligonucleotide II:

CK1
5' TGC AGC ATC AGCC 3'
Oligonucleotide III:

5' AG GTC CAG CTG CAG GAG TCT GG 3'
      G A A         C    A
           PstI
              VH1 BACKWARD

Oligonucleotide IV:

5' GAC ATT CAG CTG ACC CAG TCT CCA 3'
          PvuII
                 VK1 BACKWARD

Oligonucleotide V:

VK1FORWARD
5'GTT AGA TCT CCA GCT TGG TCC C 3'
       Bgl II
```

2. cDNA Synthesis

RNA was prepared from about $3 \times 10^8$ cells of the particular hybridomas which secrete MAb A, B, C or D, and poly $A^+$ mRNA was enriched from the latter using oligo dT Sepharose. The poly $A^+$ mRNA was used for the cDNA synthesis. The first strands of cDNA were synthesized using oligonucleotide primers which hybridize in the J region of the $V_H$ nucleotide sequences (oligonucleotide I) and at the 5' end of the kappa C gene nucleotide sequences (oligonucleotide II).

The RNA is then decomposed by NaOH treatment. The second strands of cDNA were synthesized using oligonucleotide primers which hybridize at the 5' ends of the $V_H$ (oligonucleotide III) and of the $V_{kappa}$ (oligonucleotide IV) nucleotide sequences.

3. Amplification of the Synthesized cDNA and Sequencing of the Variable Domains

The DNA generated as described in 2. was amplified using oligonucleotides I, III, IV and V (oligonucleotide V hybridizes in the J region of the $V_{kappa}$ nucleotide sequences) and the Taq DNA polymerase from *Thermophilus aquatius*. A typical mixture contained in 50 ll total volume 5 ll of ds DNA (prepared in 2.), 25 pmol of amplimers, and was 250 lM in each of DATP, dTTP, dCTP and dGTP, 67 mM tris-HCl pH 8.8, 17 mM $(NH_4)_2SO_4$, 10 mM $MgCl_2$, 200 lg/ml gelatin and 2 units of Taq polymerase. A layer of liquid paraffin was placed on the mixture and then 25 cycles each of 1 min at 95° C. (for denaturation), 1 min at 30° C. (hybridization) and 2 min at 72° C. (DNA synthesis) were carried out using a Techne PHC-1 programmable heating block.

The oligonucleotides used for the cDNA cloning and amplification contain restriction cleavage sites. The cDNA cloning and the amplification resulted in these restriction cleavage sites being introduced at the 5' end and at the 3' end of the $V_H$ and $V_{Kappa}$ nucleotide sequences (Pst I and BstEII in $V_H$ and PvuII and BglII in $V_{Kappa}$).

These restriction cleavage sites were then used to clone $V_H$ and $V_K$ cDNA fragments in M13 vectors (Lys 19, Lys 17) (Verhoyen et al. Science 239, (1988), 1534–1536).

Finally, the nucleotide sequences of the particular $V_H$ and $V_{Kappa}$ cDNA fragments were determined using the method of Sanger (PNAS, USA, 74, 5463–5467, (1977)) from the Lys 19 and Lys 17 vectors (see Tab. 7, 8, 9, 10).

Examples 4 and 5 shall explain the use of the MAb C described using MAb C:

Example 4

Mab C was fixed to the wells of microtitration plates (Nunc) by adsorption. Into these wells 20 µl sample plus 100 µl buffer-solution (OSND, Behringwerke A G) each was pipetted and 2 respective 3 hours incubated. After threefold washing with diluted Enzygnost$^R$ washing solution (OSEN, Behringwerke A G) 100 µl conjugate-solution was filled into each well. Used here were conjugates of peroxidase with lectin (e.g. wheat germ agglutinin WGA) or with other antibodies recognizing different epitopes of the tumor-associated antigens defined by MAb C. The following two or three hours incubation step at 37° C. was terminated by 3 wash cycles. For the third incubation step at room temperature 100 µl each of a buffer/substrate-chromogene solution (OUVG/OUSF Behringwerke A G) was filled into the wells and the enzyme reaction was terminated after 30 min. with 100 µl of stopping solution Enzygnost$^R$ (OSFA, Behringwerke A G). Absorbance of the samples was measured at 450 mm.

Result:

The absorbance values determined as shown above correspond to the concentration of the antigen(s) in the samples.

Figure 1:
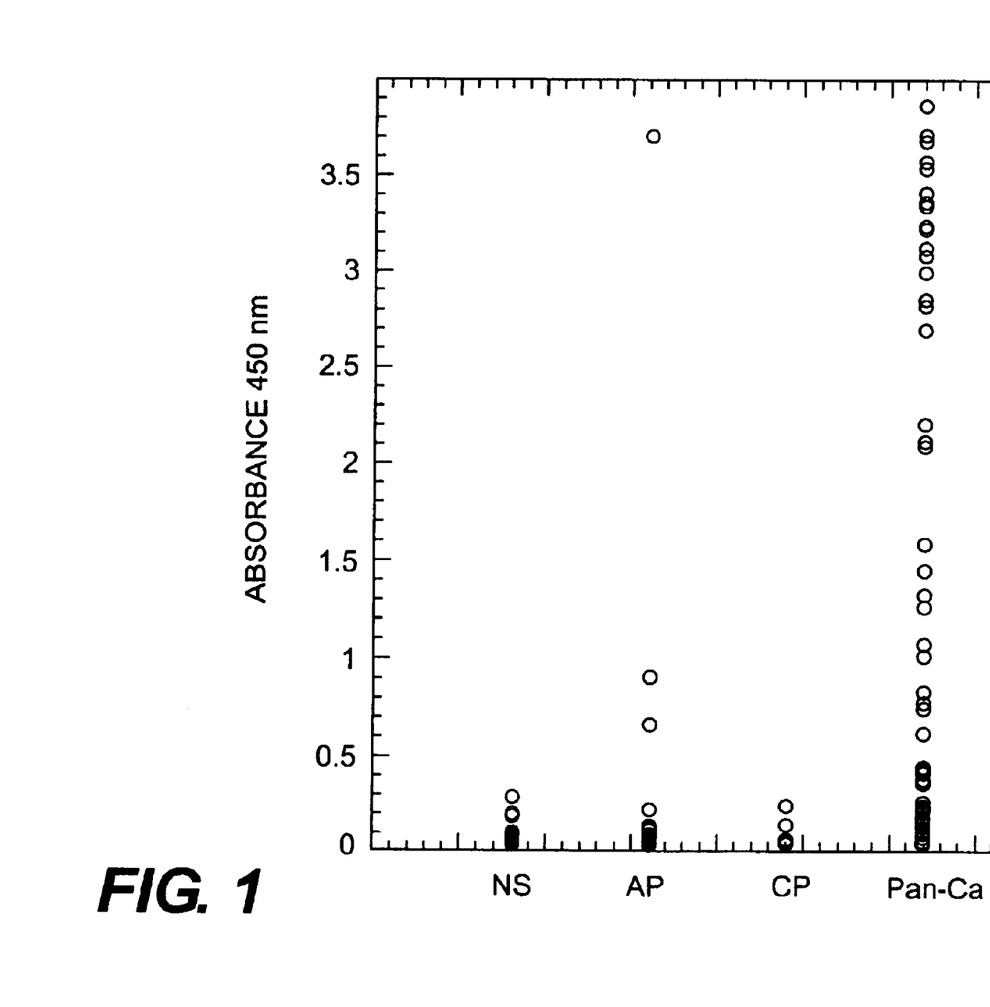

The concentration of the antigen defined by the specific binding of MAb C, in serum or plasma of tumor patients is significantly elevated as compared to said concentration of healthy control persons or patients with benign disease. This is especially true for patients with carcinoma of the pancreas (FIG. 1), significantly elevated concentrations were also determined in serum or plasma of patients with carcinoma of the stomach, colon or rectum. Equally good results were obtained irrespective of the conjugate system (antibody-peroxidase or WGA-peroxidase). With the use of MAb C as specific binding-component a sensitive test for tumor markers of especially gastrointestinal tumor disease can be made.

Example 5

5 µg each of MAb C or MAb C 50 as control (Pharmacia; Holmgren et al. (1984) British Med. J. 288, 1479) were pipeted in 50 µl phosphate-buffered-saline (PBS) into a CA 19-9 Test (CA 19-9 EIA "Roche"). The highest standard (100 U/ml) was added before start of the incubation. The tests were performed according to the instructions of the test-kit above and the absorbances of the respective samples were determined.

Figure 2:
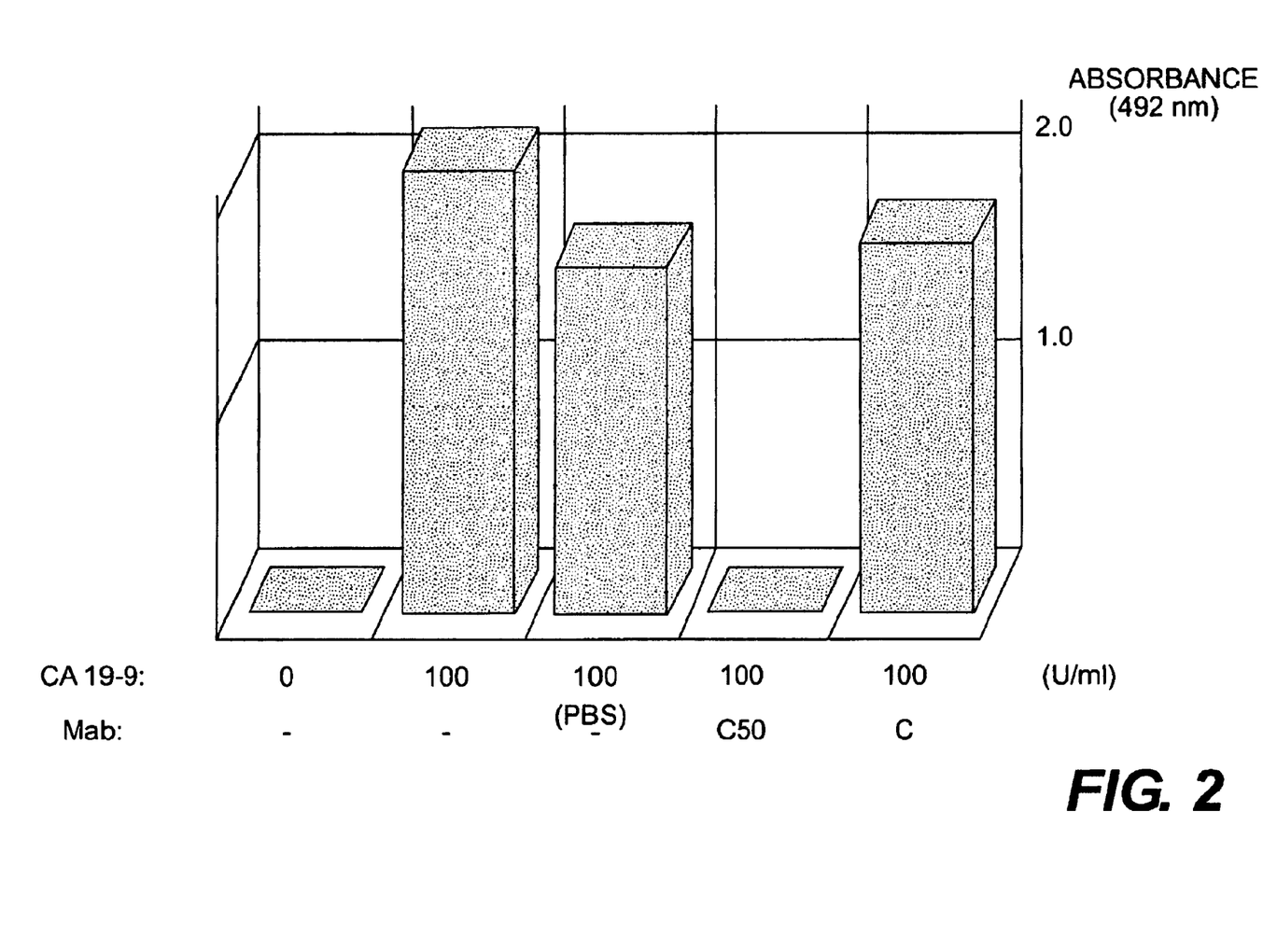
FIG. 2, Competition of CA 19-9, C50 and Mab C. Ca 19-9 means MAb Ca 19-9.

Result:

As shown in FIG. 2, the additional dilution of the standard-antigen after addition of the PBS-solution reduces the signal of the highest standard even without addition of MAb. No further reduction of the signal results by the presence of MAb C in the assay. In contrast hereto the signal formation is totally inhibited by MAb C 50, which as is known, binds among others specifically to the epitope "sialosyl Le$^{an}$" recognized also by MAb 19-9: From the above one may conclude that MAb C recognizes a different epitope as MAb 19-9.

Figure 3:
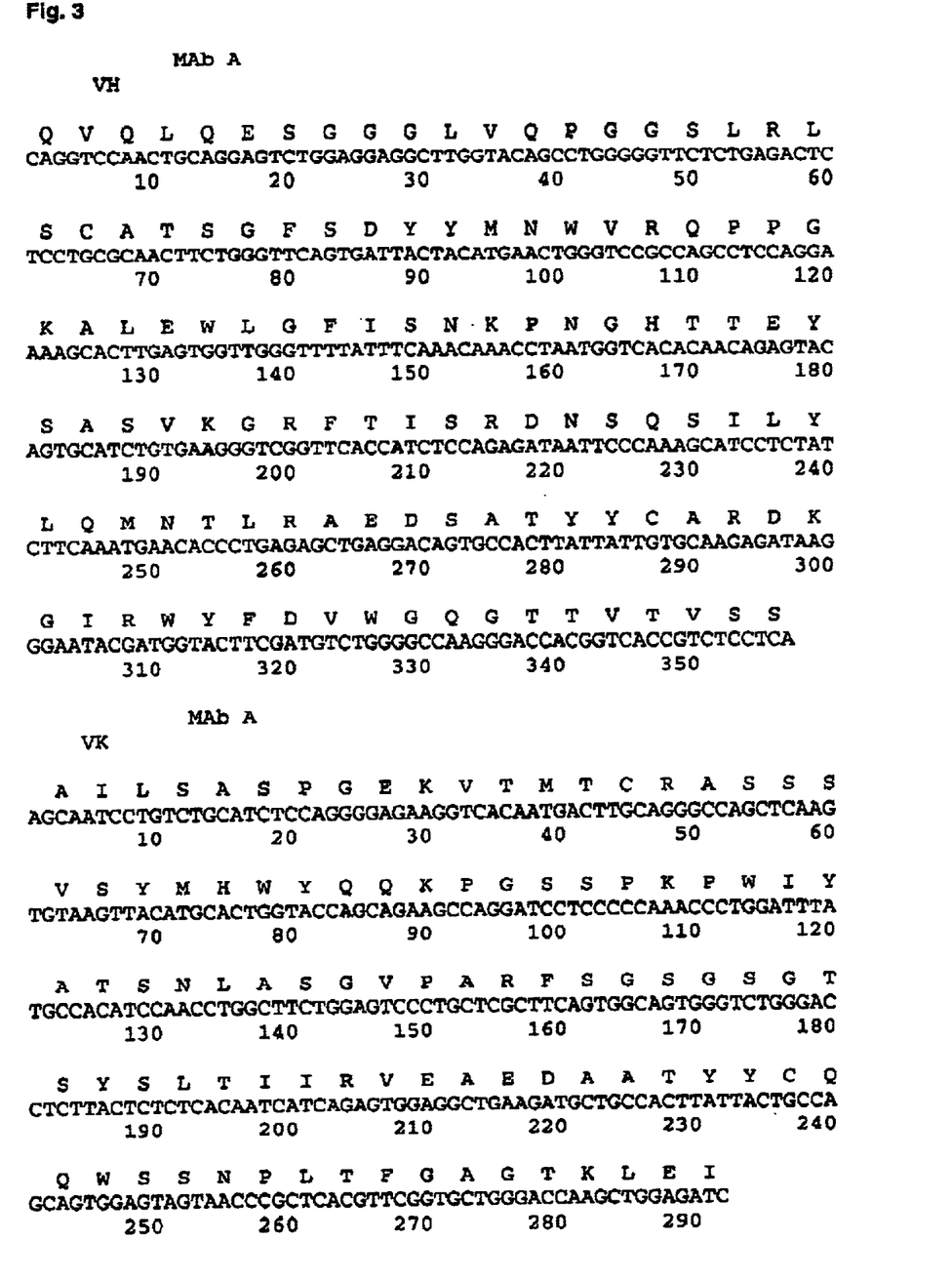
FIG. 3, Nucleotide sequences and amino acid sequences of the variable heavy Ig chain ($V_H$) and the variable light Ig chain ($V_K$) of MAb A.
Figure 4:
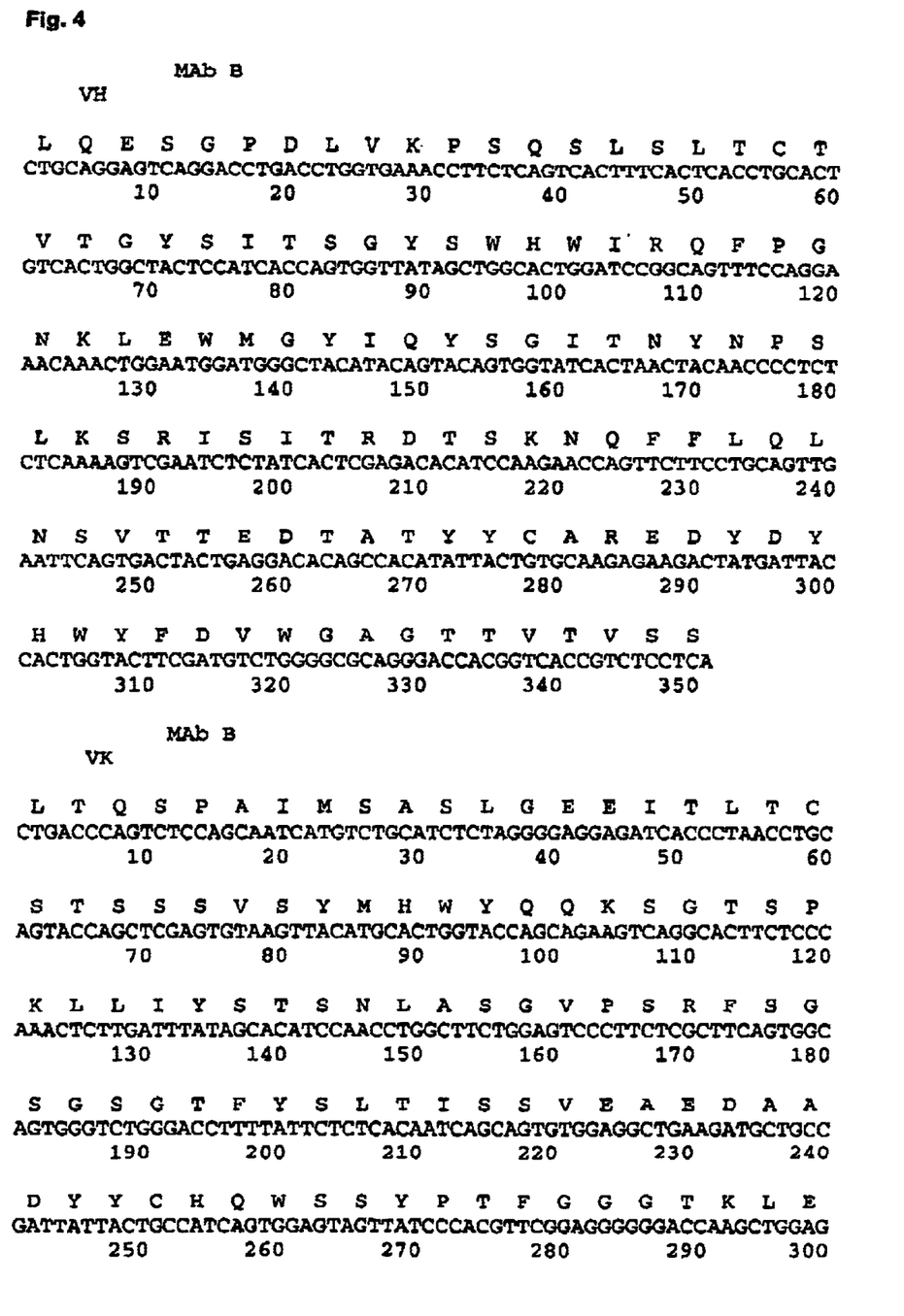
FIG. 4, Nucleotide sequences and amino acid sequences of the variable heavy Ig chain ($V_H$) and the variable light Ig chain ($V_K$) of MAb B.
Figure 5:
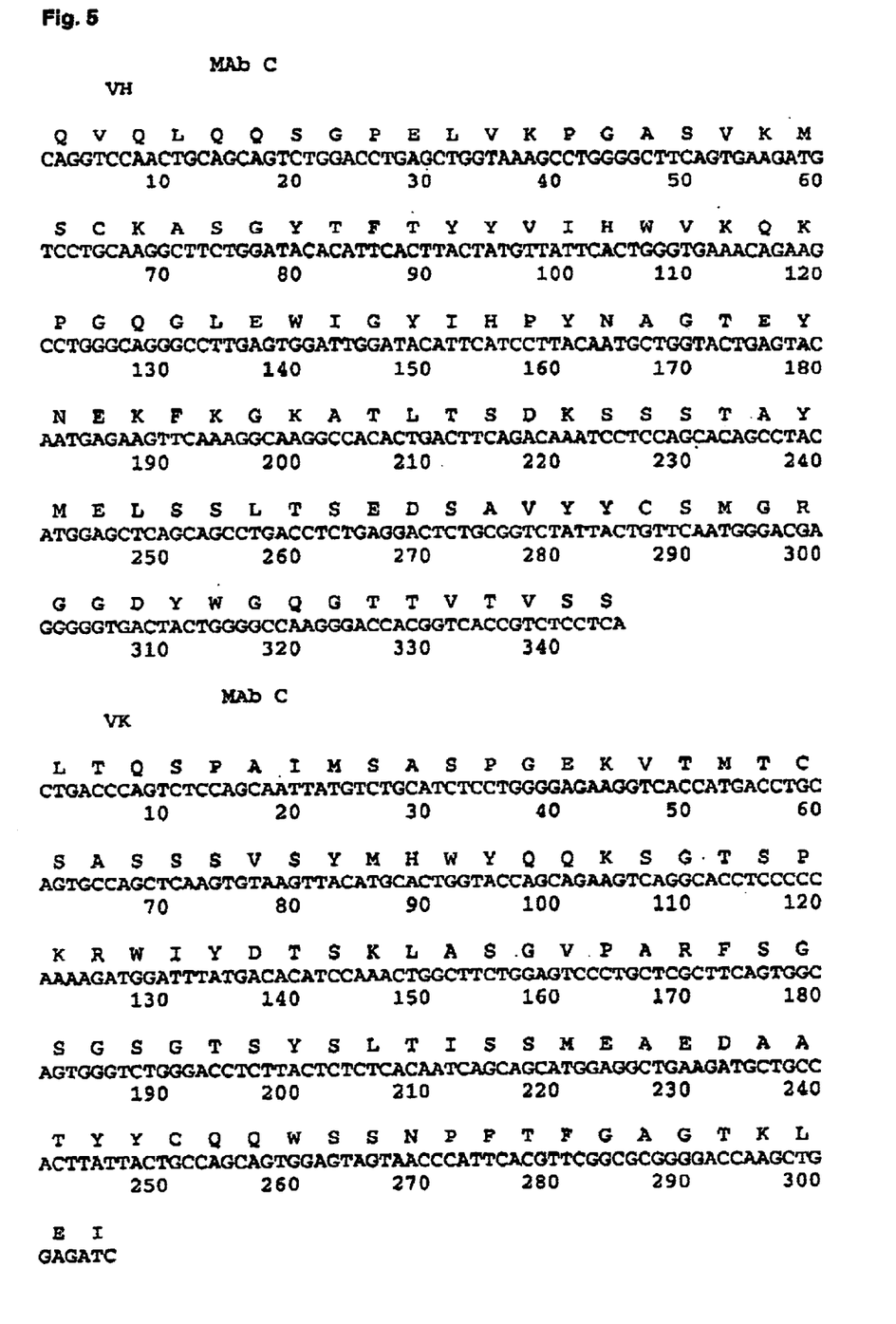
FIG. 5, Nucleotide sequences and amino acid sequences of the variable heavy Ig chain ($V_H$) and the variable light Ig chain ($V_K$) of MAb C.
Figure 6:
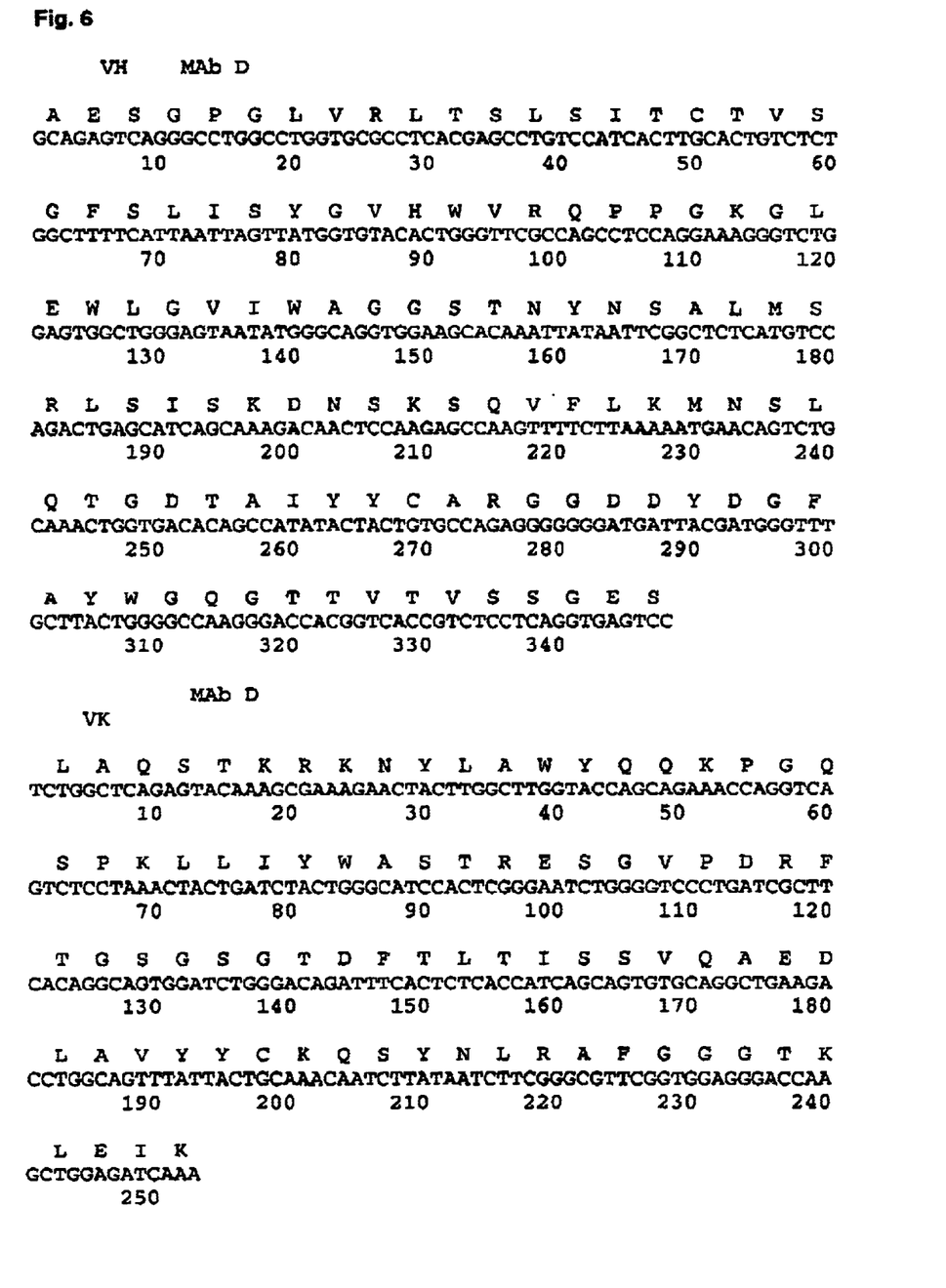
FIG. 6, Nucleotide sequences and amino acid sequences of the variable heavy Ig chain ($V_H$) and the variable light Ig chain ($V_K$) of MAb D.

What is claimed is:

1. A chimeric monoclonal antibody comprising variable $V_H$ and $V_K$ regions wherein said $V_H$ and $V_K$ regions comprise the amino acid sequences shown in FIG. 3 or 4 or 5 and in which the constant regions are human antibody amino acid sequences.

2. The monoclonal antibody of claim 1, wherein the variable regions have amino acid sequences shown in FIG. 3.

3. The monoclonal antibody of claim 1, wherein the variable regions have amino acid sequences shown in FIG. 4.

4. The monoclonal antibody of claim 1, wherein the variable regions have amino acid sequences shown in FIG. 5.

5. The monoclonal antibody as claimed in claim 1, wherein enzymes or radioactive labels are coupled to the antibody.

6. The monoclonal antibody as claimed in claim 1, wherein the antibody is coupled to toxins, catalytic antibodies, combinations of V genes of various specificities, MHC class I antigens or MHC class II antigens, or cytolytic components.

7. A pharmaceutical composition comprising the monoclonal antibody as claimed in claim 1 in a pharmaceutically acceptable carrier.

8. A monoclonel antibody as claimed in claim 1 for use in vivo or in vitro diagnosis.

9. A therapeutic composition comprising the antibody as claimed in claim 1 and an inert vehicle.

10. A method of producing the monoclonal antibody as claimed in claim 1 comprising:

a) preparing DNA encoding said variable regions and said regions outside of the variable regions containing human antibody amino acid sequences and amplifying said DNA via polymerase chain reaction (PCR) using TAQ polymerase and PCR primers from cDNA isolated from hybmidomas;

b) expressing said DNA to produce said antibody; and c) isolating said antibody.

* * * * *